(12) United States Patent
Boyette et al.

(10) Patent No.: US 6,274,534 B1
(45) Date of Patent: Aug. 14, 2001

(54) CONTROL OF KUDZU WITH A FUNGAL PATHOGEN DERIVED FROM *MYROTHECIUM VERRUCARIA*

(75) Inventors: Clyde D. Boyette, Leland; Hamed K. Abbas, Greenville, both of MS (US); Harrell L. Walker, Ruston, LA (US)

(73) Assignees: The United States of America as represented by the Secretary of Agriculture, Washington, DC (US); Louisiana Tech University Foundation, Inc., Reston, LA (US)

( * ) Notice: Subject to any disclaimer, the term of this patent is extended or adjusted under 35 U.S.C. 154(b) by 0 days.

(21) Appl. No.: 09/631,551

(22) Filed: Aug. 3, 2000

(51) Int. Cl.[7] .................................................. A01N 63/04
(52) U.S. Cl. ............................................... 504/117
(58) Field of Search .............................. 504/117

(56) References Cited

PUBLICATIONS

Nesmith, Jeff. "Ivy league bout is a death match: Fungus found to kill kudzu". Washington Times. p. A1, Feb. 2000.*

* cited by examiner

*Primary Examiner*—S. Mark Clardy
(74) *Attorney, Agent, or Firm*—M. Howard Silverstein; Joseph A. Lipovsky; John D. Fado

(57) ABSTRACT

Methods for the biological control of kudzu (*Pueraria lobata*) using the fungus *Myrothecium verrucaria* have been developed. In typical applications, conidia of the fungus are applied by means of a liquid surfactant to kudzu in amounts effective to produce plant lesions which kill or suppress the kudzu. A strain of *M. verrucaria* is on deposit with the Department of Biological Sciences, Louisiana Tech University in Ruston, La., and with the patent collection of the International Mycological Institute in surrey, UK, where it has been assigned deposit number IMI 368023.

5 Claims, No Drawings

CONTROL OF KUDZU WITH A FUNGAL PATHOGEN DERIVED FROM *MYROTHECIUM VERRUCARIA*

BACKGROUND OF THE INVENTION

1. Field of the Invention

Kudzu (*Pueraria lobata*) is a perennial leguminous vine introduced from Japan that produces a large starchy tuber-like root system. Now infesting over 7 million acres of the southeastern United States, and spreading at a rate of 120, 000 acres per year, this plant represents a serious threat to productivity in its growing region.

This invention relates to novel methods for the control of kudzu based upon the application of conidia of *Myrothecium verrucaria* in herbicidally effective amounts. These methods, due to their systemic nature, do in fact provide superior control of the weed as compared to known commercial alternatives.

2. Description of the Prior Art

Several methods are known in the art for using microorganisms to control weeds and other pest plants. As disclosed in U.S. Pat. No. 3,999,973 (Daniel et al.), the anthracnose fungus *Colletotrichum gloeosporiodes* has been used to control the weed northern jointvetch and another strain of the fungus has been used to control winged waterprimrose. *Colletotrichum malvarum* has been used to control prickly sida. These three pathogens have been combined to control all three target weeds at once. In other experimental work, the fungus *Alternaria macrospora* has been used to control spurred anoda (*Anoda cristata*) [H. L. Walker, *Weed Science*, Vol.29, pp.505–507, 1981].

Research activity involving *M. verrucaria* is noted on page 8 of the IBG News, Vol.4, No. 1, May 1995 issue. U.S. Pat. No. 4,390,360 (Walker), describes "Control of Sicklepod; Showy Crotaria and Coffee Senna With a Fungal Pathogen" using a specific host strain of the fungus *Alternaria cassiae* to produce typical weed lesions which kill or suppress the respective weeds. U.S. Pat. No. 4,419,120 (Walker), discloses "Control of Prickly Sida, Velvetleaf, and Spurred Anoda With Fungal Pathogens" using a specific host strain of the fungus *Fusarium lateritium* to kill or suppress the respective weeds. U.S. Pat. No. 4,715,881 (Andersen et al.), details "Control of Eastern Black Nightshade With a Fungal Pathogen" using a strain of *Colletotrichum coccodes* which is pathogenic towards eastern black nightshade (*Solanium prycanthum*). U.S. Pat. Nos. 4,718,935 and 4,767,441 (Walker et al.), describe a "Method for the Preparation of Mycoherbicide-Containing Pellets" characterized by alginate gel pellets containing living fungus capable of producing conidia when exposed to sufficient light and moisture. U.S. Pat. Nos. 4,724,147 and 4,818,530 (Marois et al.), detail the "Preparation of Pellets Containing Fungi for Control of Soilborne Diseases", in which fungi are first selected and grown for a time sufficient to produce inoculum. The fungal propagules are harvested, homogenized and diluted with sodium alginate solution. Pelletization is then accomplished by dropwise addition of the fungal propagule-alginate mixture into a solution of calcium chloride or calcium gluconate. The resulting alginate gel pellets containing living fungi can then be dried and used to inoculate agricultural fields infested with soilborne plant diseases. U.S. Pat. No. 5,192,541 (Savage et al.), describes "Weed-killing *Xanthamonas campestris*", in which novel microorganisms useful in controlling unwanted grasses and other weeds are discovered through a unique process which involves isolating plant pathogens from asymptomatic plants. U.S. Pat. No. 5,393,728 (Charudatten et al.), details a "Broad Spectrum Bioherbicide to Control Several Species of Pigweeds", in which a novel Phomopsis sp. fungus is used as an effective broad-spectrum bioherbicide for controlling pigweed.

U.S. Pat. No. 5,747,029 (Walker et al.), hereby incorporated by reference, teaches methods for the biological control of various weeds including sicklepod, pigweed, spurred anoda, jimsonweed, and hemp sesbania using the fungus *M. verrucaria* . This work, while showing that *M. verrucaria* is effective in controlling a number of varieties of weeds in several different types of important agricultural crops, shows that effective control of a given species is more the exception than the rule and that the host range for this fungus was not predictable (Col. 2, lines 66–67). Effective control, where it occurred, also required the presence of a dew period. The prior art as a whole teaches that fungi developed as biological herbicides should be restricted in host range to a limited number of plant species.

SUMMARY OF THE INVENTION

We have now discovered means for the effective biological control of kudzu (*Pueraria lobata*) using the fungus *M. verrucaria*. The fungus is isolated, produced, compositioned and applied to kudzu by methodology taught in U.S. Pat. No. 5,747,029 (Walker et al.), which is herein incorporated by reference.

In accordance with this discovery, it is an object of the invention to provide means for the effective biological control of kudzu.

Other objects and advantages of the invention will become readily apparent from the ensuing description.

DEPOSIT OF BIOLOGICAL MATERIAL

*M. verrucaria*(Alb. and Schwein) Ditmar ex Fr. is on deposit with the Department of Biological Sciences, Louisiana Tech University in Ruston, La., at the United States Department of Agriculture, Agricultural Research Service, Southern Weed Science Research Unit in Stoneville, Miss.; and was placed on deposit with the International Mycological Institute, Bakeham Lane, Egham Surrey, UK, on May 18, 1994, as IMI number 361690. The deposit was placed in the patent collection of the International Mycological Institute on Jun. 21, 1995, under the terms of the Budapest Treaty, and has been assigned accession number IMI 368023.

According to M. Tulloch, (The Genus Myrothecium Tode ex Fr. *Mycologiical Papers* 130, 1–42, 1972), *M. verrucaria* is described as follows: "Spore mass wet, black, convex surrounded by wet floccose margin. Spores broadly fusiform, one end pointed the other protruding and truncate, in erythrosin and $NH_4$ solution with a fantailed appendage on the pointed end, 6.5–8×2.3–5 microns."

The *M. verrucaria* used in this invention was isolated from diseased plants of sicklepod, a new host record for this fungus.

DETAILED DESCRIPTION OF THE INVENTION

The fungus may be cultured by conventional means, such as those disclosed in U.S. Pat. No. 5,747,029 (Walker), hereby incorporated by reference. Conidia produced are then formulated in aqueous solution and compositioned with a surfactant such as Silwet L-77 (trademark); a silicone-polyether copolymer spray adjuvant, OSI Specialties, Inc., Charlotte, N.C. Other useable surfactants include Tween-20

[oxysorbic (20 POE) (polyoxyethylene sorbitan monooleate)], Tween-80 (Polysorbate 80) and Sterox [nonoxynol (9 to 10 POE) [a-(p-onylphenyl)-w-hydroxypoly(oxyethylene)]]. Useable compositional concentrations of the conidia range from about $2 \times 10^6$ to about $2 \times 10^8$ conidia/ml of solution, with the surfactant being present in amounts ranging from about 0.02% to about 0.4% (vol/vol), preferably about 0.1 to about 0.3% (vol/vol). Application is made to the kudzu at a rate ranging from about 5 to about 100 gallons per acre, preferably about 40 to about 60 gallons per acre. Effective control of the kudzu is herein defined as achieving a biocidal rate of 90% or greater within 14 days of application. Efficacy does not require the presence of a dew period as indicated by growth chamber and greenhouse tests, and is similarly tolerant under field conditions to temperatures up to about 40° C.

The experimental parameters used in examples cited for this invention are not intended to limit the scope of this invention. Modification of factors such as inoculum concentrations, parameters for inoculum production, surfactants, application methods, and other factors, would be expected to influence efficacy of this invention. Parameters were selected to enable detection of interactions, to document the relationship of this invention to the prior art, and to illustrate that the unique and surprising characteristics of this invention were not obvious and could not have been predicted from the prior art.

EXAMPLE 1

Inoculum Production

Inocula (conidia) of *M. verrucaria* for all experiments were produced in petri dishes containing Difco potato dextrose agar (PDA). Agar surfaces were flooded with 1 ml of a *M. verrucaria* conidia suspension containing $2 \times 10^6$ conidia/ml. The dishes were inverted on open-mesh wire shelves and incubated at 25° C. for 5 days in fluorescently lighted incubators. The resulting conidia were rinsed from the cultures with sterile, distilled water, and were adjusted to the desired concentrations by adding distilled water. Conidia counts and concentrations were estimated with hemacytometers. PDA inoculated with conidial suspensions produced fungal lawns after 5 days. When conidia were harvested by flooding the cultures with 10 ml of distilled water, each culture produced approximately $8 \times 10^8$ conidia.

Test Plant Propagation

Kudzu seedlings were grown from seed in 10 cm plastic pots containing a 1:1 (w/w) commercial potting mix/soil combination supplemented with a controlled release 13:13:13 (N:P:K) fertilizer. Temperatures in the greenhouse ranged from 28° C. to 32° C. with 40 to 60% relative humidity. The photoperiod was approximately 14 hours, with 1600 to 1800 $\mu mol/m^2/s$ photosynthetically active radiation (PAR) at midday, as measured with a light meter.

Effect of Inoculum Concentration and Plant Growth

Seedlings in either the cotyledonary, first-to-third leaf, fourth-to-sixth leaf, or seventh-to-eighth leaf growth stage were inoculated by aerosol sprayers until foliage was fully wetted with either 0, $2 \times 10^5$, $2 \times 10^6$, $2 \times 10^7$, or $2 \times 10^8$ conidia/ml contained in 0.2% Silwet 1-77 surfactant. Following inoculation, the plants were incubated on greenhouse benches and monitored for disease development. Greenhouse lighting and temperature conditions were as described previously. Experimental units consisted of groups of 10 plants. The treatments were replicated three times and the experiment was conducted twice. A randomized complete block experimental design was utilized, and the data were analyzed using regression analysis and 95% level confidence limits.

As shown in Table I, mortality was significantly increased at all growth stages by increasing the inoculum concentration. Greater overall mortality was achieved with inoculum concentrations of $2 \times 10^7$ and $2 \times 10^8$ conidia/ml than with lower concentrations tested. An inoculum concentration of $2 \times 10^6$ conidia/ml killed 40–50% of the weeds in the cotyledonary growth stage, but was less efficacious on larger plants. Seedlings in the cotyledonary, first to third leaf, and fourth to sixth leaf stages were effectively killed with $1 \times 10^7$ conidia/ml, but larger plants required an order of magnitude larger inoculum concentration to be 90% controlled.

TABLE I

Effect of Plant Growth Stage and Inoculum Concentration on Control of Kudzu by *Myrothecium verrucaria* Kudzu Mortality (%)[1]

| Number of Leaves | Inoculum Concentration (Spores/ml)[2] | | | | | |
|---|---|---|---|---|---|---|
| | 0 | $2 \times 10^4$ | $2 \times 10^5$ | $2 \times 10^6$ | $2 \times 10^7$ | $2 \times 10^8$ |
| Cotyledon | 0 | 10(4) | 12(3) | 48(6) | 100 | 100 |
| 1–3 | 0 | 5(3) | 6(0) | 35(5) | 94(4) | 100 |
| 4–6 | 0 | 0 | 0 | 35(4) | 85(6) | 95(4) |
| 7–8 | 0 | 0 | 0 | 21(4) | 60(5) | 84(5) |

[1]Values represent an average obtained from two experiments with groups of 10 plants in each experiment. Values in parentheses are standard mean errors.
[2]Kudzu plants were sprayed until runoff occurred.

Effect of Incubation Temperature

Kudzu plants in the cotyledonary to first true leaf stages of growth were inoculated by aerosol sprayers until the foliage was fully wetted with suspensions containing $2 \times 10^7$ conidia/ml plus 0.2% Silwet L-77 surfactant. Control plants were sprayed with 0.2% surfactant only. Immediately following inoculation, the plants were placed in Shearer (Rheem Mfg. Co., Weaverville, N.C.) growth chambers at constant day/night temperatures of 10° C., 15° C., 20° C., 25° C., 30° C., 35° C. or 40° C. Photoperiods were 14 hour day/10 hour night with approximately 900 $\mu mol/m^2/s$ PAR. Disease development was monitored daily. After 14 days following inoculation all 10 plants of each experimental unit, both living and dead, were excised at the soil line, combined, and dried (80° C. for 7 days) for dry weight determinations. A randomized complete block experimental design was utilized, and the data were analyzed using 95% confidence limits.

As shown in Table II, pathogenesis and mortality occurred at all temperatures that were tested. Higher temperatures promoted greater disease development and weed control. Disease symptomatology was characterized by necrotic flecking which occurred within 6 hours following treatment at incubation temperatures of 30–40° C. with slower disease development at lower temperatures. Disease symptoms progressed from inoculated cotyledons and leaves to produce stem lesions within 48 hours. This indicates that the invention could be used even in midsummer when similar temperatures in kudzu-infested regions of the southeastern United States occur.

TABLE II

Effect of Incubation Temperatures on Mortality and Dry Weight Reduction of Kudzu by *Myrothecium verrucaria*[1]

| Incubation Temp. (° C.) | Kudzu Mortality (%)[2] | Dry Weight Reduction (%) |
|---|---|---|
| 10 | 8(4) | 10(3) |
| 15 | 18(2) | 20(4) |
| 20 | 38(5) | 42(4) |
| 25 | 72(6) | 80(5) |
| 30 | 92(4) | 95(3) |
| 35 | 100(0) | 100(0) |
| 40 | 100(0) | 100(0) |

[1]Plants in the cotyledonary stage of growth sprayed until runoff occurred at a concentration of $2.0 \times 10^7$ spores/ml.
[2]Values represent an average obtained from two experiments with groups of 10 plants in each experiment. Values in parentheses represent mean standard errors at $p = 0.05$.

Field Experiments

Kudzu seedlings in the cotyledonary to first leaf growth stage were transplanted into 0.5 m² field microplots in separate experiments. Each plot consisted of 10 seedlings. The plants were allowed to acclimate to field conditions for one week prior to treatment. Treatments consisted of $2 \times 10^7$ conidia/ml in distilled water, $2 \times 10^7$ conidia/ml in 0.2% Silwet L-77, distilled water only, and 0.2% Silwet L-77 only. The plants were sprayed until fully wetted (approximately 3 ml/plant). Applications were made at midday with a hand-held pressurized sprayer. The plants were monitored for disease development at 5 day intervals for 15 days, then harvested for dry weight determinations as described previously for the growth chamber experiments. A randomized complete block design was utilized, and the treatments were replicated three times. Data from the two experiments were pooled following subjection to Bartlett's test for homogeneity (Steele and Torrey, 1980) and were analyzed using the analysis of variance. Treatment means were separated using Duncan's multiple range test.

In the microplot experiments, kudzu plants treated with the fungus/surfactant mixtures exhibited leaf and stem necrosis within 24 hours following inoculation, with mortality occurring within 96 hours. After 7 days, 100% of the inoculated plants had been killed in plots treated with *M. verrucaria*/Silwet L-77 mixtures. The fungus sporulated profusely on infected tissue and was easily reisolated. No visible damage was observed on plants in plots treated with the fungus in distilled water only, 0.2% Silwet L-77 only, or untreated controls, and no dry weight reductions occurred in any of these treatments.

EXAMPLE 2

A field test was established in a site that was heavily infested with a naturally occurring kudzu population. The plants were vigorous and had not yet flowered. Treatments consisted of: 1) $2 \times 10^6$ conidia/ml in distilled water; 2) $2 \times 10^7$ conidia/ml in distilled water; 3) $2 \times 10^6$ conidia/ml in 0.2% Silwet L-77 surfactant; 4) $2 \times 10^7$ conidia/ml in 0.2%,Silwet L-77 surfactant; 5) 0.2% Silwet L-77 surfactant only, and 6) untreated control. Spray volumes were applied at 450 L/hectare with backpack sprayers. Visual ratings based the percentage of necrotic kudzu tisses in treated plots as compared to untreated control plots were used to assess weed control at weekly intervals for 4 weeks. The test was arranged in a completely randomized design with 3 replications.

Kudzu was controlled 100% after 14 days in plots treated with fungus/surfactant mixtures applied at $2 \times 10^7$ conidia/ml, with no visual symptoms or weed control occurring in any other treatment. After 4 weeks, vines from untreated plot margins had begun to spread into treated areas where kudzu had been defoliated, but no new leaf growth occurred on vines that had been considered "killed".

While the preferred embodiments have been described above, it will be recognized and understood that various modifications may be made in the invention and the appended claims are intended to cover all such modifications which may fall within the spirit and scope of the invention.

We claim:

1. A method for the biological control of kudzu comprising the application of a herbicidally effective amount of *Myrothecium verrucaria* thereto.

2. The method of claim 1 wherein said *Myrothecium verrucaria* is applied in the form of an aqueous composition containing a liquid surfactant.

3. The method of claim 2 wherein said surfactant is selected from the group consisting of a silicone-polyether copolymer spray adjuvant, oxysorbic (20 POE) polyoxyethylene sorbitan monooleate, Polysorbate 80 and nonoxynol (9 to 10 POE).

4. The method of claim 1 wherein said *Myrothecium verrucaria* has the identifying characteristics of strain IMI 368023.

5. The method of claim 1 wherein said *Myrothecium verrucaria* is applied in the form of conidia.

* * * * *